United States Patent
Tuman et al.

(10) Patent No.: US 7,014,906 B2
(45) Date of Patent: Mar. 21, 2006

(54) HOOK FASTENER AND METHOD OF MAKING

(75) Inventors: Scott J. Tuman, Woodbury, MN (US); Jayshree Seth, Woodbury, MN (US); Timothy J. Lindquist, Woodbury, MN (US); Troy K. Ista, River Falls, WI (US); Ronald W. Ausen, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 223 days.

(21) Appl. No.: 10/686,324

(22) Filed: Oct. 14, 2003

(65) Prior Publication Data

US 2005/0079321 A1    Apr. 14, 2005

(51) Int. Cl.
*B32B 3/06* (2006.01)
(52) U.S. Cl. .................................................. 428/100
(58) Field of Classification Search .......... 428/98–101, 428/109, 134, 110, 90; 24/452, 662, 584.1; 442/57, 329, 35, 333; 604/391, 385.04; 264/145, 147
See application file for complete search history.

(56) References Cited

U.S. PATENT DOCUMENTS

| | | | |
|---|---|---|---|
| 3,266,113 A | 8/1966 | Flanagan, Jr. | |
| 3,485,706 A | 12/1969 | Evans | |
| 3,533,892 A | 10/1970 | Kantorowicz | |
| 3,557,413 A | 1/1971 | Engle | |
| 4,001,366 A | 1/1977 | Brumlik | |
| 4,056,593 A | 11/1977 | de Navas Albareda | |
| 4,189,809 A | 2/1980 | Sotos | |
| 4,302,495 A | 11/1981 | Marra | |
| 4,612,226 A | 9/1986 | Kennette et al. | |
| 4,775,579 A | 10/1988 | Hagy et al. | |
| 4,894,060 A * | 1/1990 | Nestegard | 604/391 |
| 5,058,472 A | 10/1991 | Kakko-Chiloff | |
| 5,100,400 A | 3/1992 | Mody et al. | |
| 5,334,446 A | 8/1994 | Quantrille et al. | |
| 5,392,498 A | 2/1995 | Goulait et al. | |
| 5,393,599 A | 2/1995 | Quantrille et al. | |
| 5,431,991 A | 7/1995 | Quantrille et al. | |
| 5,467,678 A | 11/1995 | Stollenwerk | |
| 5,891,549 A | 4/1999 | Beretta et al. | |
| 6,209,177 B1 | 4/2001 | Murasaki | |
| 6,367,128 B1 * | 4/2002 | Galkiewicz et al. | 24/585.1 |
| 6,484,371 B1 * | 11/2002 | Romanko et al. | 24/306 |
| 6,737,147 B1 * | 5/2004 | Kennedy et al. | 428/100 |

(Continued)

FOREIGN PATENT DOCUMENTS

WO    WO 96/03101 A1    2/1996

(Continued)

*Primary Examiner*—Colleen P. Cooke
*Assistant Examiner*—Paul Wartalowicz
(74) *Attorney, Agent, or Firm*—William J. Bond

(57) ABSTRACT

The present invention is directed at a hook mechanical fastener/fibrous composite comprising hook elements on hook containing backing elements or a netting embedded in a fibrous web. The hook elements preferably are on backing elements that are connected or integral and can be strands oriented at angles to each other in a net form. The backing elements generally have a first outer face and a second outer face. The backing elements on at least one of the first or second outer faces have a plurality of hook elements. The hook containing backing elements are embedded within a fibrous web, preferably by hydroentangling the fibers around the backing element, preferably without use of auxiliary attachment means such as adhesives or point bonding.

36 Claims, 7 Drawing Sheets

U.S. PATENT DOCUMENTS

2001/0016245 A1   8/2001   Tuman et al.
2002/0166573 A1   11/2002  Policicchio et al.
2003/0009144 A1   1/2003   Tanzer et al.
2003/0044569 A1   3/2003   Kacher et al.
2003/0049407 A1   3/2003   Kacher et al.

FOREIGN PATENT DOCUMENTS

WO    WO 02/096233 A1   12/2002

* cited by examiner

HOOK FASTENER AND METHOD OF MAKING

SUMMARY OF THE INVENTION

The present invention concerns a mesh, netting or strand element including hook fasteners incorporated into a fibrous web for use with hook and loop fasteners.

Hook type mechanical fasteners typically have backing formed from relatively thick and rigid backing materials. Recent attempts in the art suggest that flexible backings are desirable for hook fasteners and have proposed hooks or discrete hook patches on a flexible backing. US 2001/0016245 discloses a web of material, generally a nonwoven web, having a multiplicity of discrete polymer regions with a plurality of stems extending from each polymer region. Generally, discrete quantities of polymeric material are deposited and fused to the web by entangling or encapsulating the fibers that make up the nonwoven web, and simultaneously or subsequently formed into stems or hooks. A similar approach is also discussed in WO02/096233.

Flexible and generally breathable webs with isolated areas or patches of hook material have drawbacks. The processes of depositing the hook material onto the web are generally complicated and require precision manufacturing. The formed web material having the hook material is also generally non-uniform posing challenges for roll stability and dimensional stability during manufacturing of the continuous web itself and then delivering it as a hook component into a finished article. Moreover the webs, where hook fastening material has been configured into discrete areas, creates the potential for skin irritation due to the rigid edges associated with each discrete patch of hook material. In addition the cloth-like feel is limited to one side of the web material laminate since the hook patches are on one side of the nonwoven web.

US2003/0009144 discloses a fastening material embedded within a flexible material to help present a cloth-like surface to the wearer or the caregiver (e.g., with a diaper) and to reduce the possibility of the fastener having exposed harsh edges. The method to achieve this, is again extremely complex, requiring a large deal of precision and has the same drawbacks associated with roll stability and dimensional stability when undergoing manufacturing and converting.

U.S. Pat. No. 5,392,498 discloses an array of free formed prongs (hooks) deposited on a substrate. The substrate is stated as possibly being a film, a woven, a paper or a nonwoven. The prongs can be formed by a screen printing type of process, but the process is generally limited to use of adhesive type polymers (polyesters) and still the hooks are easily detached from the substrate due to the limited contact area.

Many articles are made at high speed in order for the process to be economical. It is thus desirable for a manufacturer of these articles, which use a mechanical fastener, to mount a roll of the hook fastener material which has uniform machine handling properties to allow high-speed application of the mechanical fasteners. This is difficult with the current proposed hook type mechanical fasteners which also provide the benefits of flexibility, softness and breathability. Moreover, there is a need for improved methods to reliably and consistently make low manufacturing cost mechanical fasteners having the combined benefits of flexibility, softness and/or breathability.

The present invention is directed at providing a novel mechanical fastening cloth-like laminate, which is economical, and, exhibits ease, simplicity and mechanical stability for use in high speed manufacturing processes, and provides the desirable functional and aesthetic properties.

BRIEF DESCRIPTION OF THE INVENTION

The present invention is directed at a hook mechanical fastener/fibrous composite comprising hook elements on hook containing backing elements or a netting embedded in a fibrous web. The hook elements preferably are on backing elements that are connected or integral and can be strands oriented at angles to each other in a net form. The backing elements generally have a first outer face and a second outer face. The backing elements on at least one of the first or second outer faces have a plurality of hook elements. The hook containing backing elements are embedded within a fibrous web, preferably by hydroentangling the fibers around the backing element, preferably without use of auxiliary attachment means such as adhesives or point bonding.

BRIEF DESCRIPTION OF THE DRAWINGS

The present invention will be further described with reference to the accompanying drawings wherein like reference numerals refer to like parts in the several views, and wherein.

DETAILED DESCRIPTION OF THE PREFERRED EMBODIMENT

Figure 1:
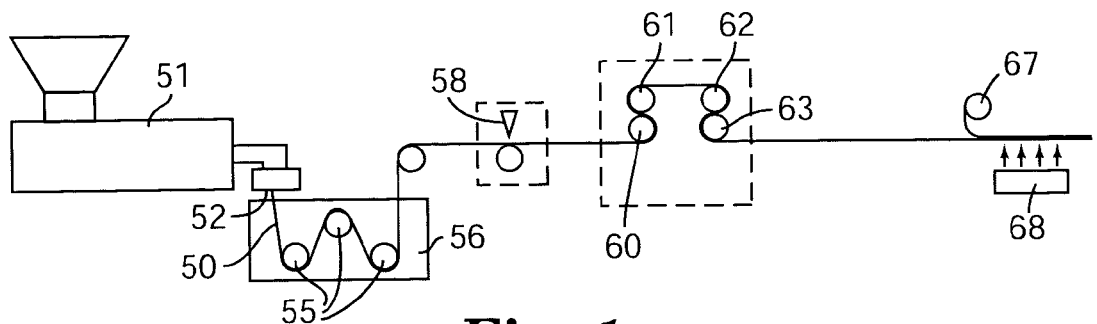
FIG. 1 schematically illustrates a method for making a hook netting such as shown in FIG. 4 and fastening web as shown in FIG. 5.

The invention hook fastener fibrous composite is formed with hook elements provided on one or more backing elements that can be in the form of a netting or strand elements. These hook element containing backing elements, for example in the form of discrete or connected strands or one or more nettings are then embedded within a fibrous web. The hook elements are preferably on strand elements that are connected so as to form a netting and oriented at angles to each other in the net form. The strands, whether isolated or partially connected strand elements or more firmly connected into a net form, generally have a first outer face and a second outer face and two side faces. The strands, on at least one of the first or second outer faces, have a plurality of hook elements. The hook containing strands are embedded within a fibrous web, e.g., a nonwoven web, preferably by hydroentangling the fibers of the nonwoven web around the strands, preferably without the use of auxiliary attachment means such as adhesives or point bonding (e.g., heat bonding, ultrasonic bonding or the like).

The nonwoven web is preferably initially made to have sufficient free fibers to be entangled around the hook containing backing element. The nonwoven could also, or in addition, be treated prior to the entangling to unbond fibers. For example, the nonwoven can be, e.g., mechanically stretched and worked (manipulated), e.g., by using grooved nips or protuberances, prior to entangling to unbond the fibers so as to provide the mobility to the fibers needed to entangle the hook containing strands. Generally, nonlimiting examples of suitable nonwoven webs include dry laid webs, carded webs, spunbond webs, meltblown webs and combinations thereof. The webs can be elastic or inelastic. The nonwoven web would have a basis weight of from 10 to 500 g/m$^2$, preferably 20 to 200 g/m$^2$, or most preferably 30 to 100 g/m$^2$.

The fibers of the nonwoven webs need not be unbonded when passed into the entangling step. However, it is necessary that during entangling there are sufficient free fibers or fiber portions (that is, the fibers or portions thereof are sufficiently mobile) to provide the desired degree of entanglement and embedding of the hook containing backing element or elements within the nonwoven web. Such fiber mobility can possibly be provided by the force of the jets during hydraulic entangling or by the structure of the nonwoven web or by mechanically or otherwise disrupting the web to create free or mobile fibers.

The hydraulic entangling technique generally involves treatment of a laminate of at least the nonwoven web or webs and the hook containing backing element or elements, while supported on an apertured support, with streams of liquid from jet devices. The support can be a mesh screen or forming wires or an apertured plate. The support can also have a pattern so as to form a nonwoven material with such pattern, or can be provided such that the hydraulically entangled nonwoven hook fastener web is non-patterned. The apparatus for hydraulic entanglement can be any conventional apparatus, such as described in U.S. Pat. No. 3,485,706, the contents of which are incorporated herein by reference in its entirety. In such an apparatus, fiber entanglement is accomplished by jetting liquid (e.g., water) supplied at pressures, for example, of at least about 200 psi (gauge), to form fine, essentially columnar, liquid streams toward the surface of the supported laminate. The supported laminate is traversed with the streams until the fibers of the nonwoven web are randomly entangled and intertwined with the hook containing backing elements. The laminate can be passed through the hydraulic entangling apparatus a number of times on one or both sides, with the liquid being supplied at pressures of from about 50 to 3000 psi (gauge). The orifices which produce the columnar liquid streams can have typical diameters known in the art, e.g., 125 microns (0.005 inches), and can be arranged in one or more rows with any number of orifices in each row. Various techniques for hydraulic entangling are described in the aforementioned U.S. Pat. No. 3,485,706, and this patent can be referred to in connection with such techniques. Other entangling techniques include mechanically entangling by needle punching. Optionally, other functional layers could be incorporated into the laminate during the entangling operation. The other layers would be foraminous or otherwise entangleable and could include knitted webs, woven webs, other functional nettings or strands or fibrous webs. This optional entangleable layer could be used to add strength, elasticity, aesthetics, advertising, softness, rigidity or other desired properties.

After the laminate has been entangled to form a composite web, it may, optionally, but not preferably, be treated at a bonding station (not shown in FIG. 1) to further enhance its strength. Such a bonding station is disclosed in U.S. Pat. No. 4,612,226, the contents of which are incorporated herein by reference. Other optional secondary bonding treatments include thermal bonding, ultrasonic bonding, adhesive bonding, combinations of bonding treatments, etc. Such secondary bonding treatments provide added strength, may also stiffen the resulting product (that is, provide a product having decreased softness) and decrease its loft, as such may not be preferred. In the preferred embodiments, all or substantially all secondary bonding is omitted or used at a level of less than 30 percent or preferably less than 15 percent and most preferably less than 5 percent of the surface area of the composite.

After the composite has been entangled, it can be dried by drying cans (or other drying means, such as an air through dryer, known in the art), and wound on a winder.

The formed invention fastener composite comprises hook containing backing elements enmeshed or embedded within a nonwoven web such that fibers of the nonwoven web are present on both outer faces of the hook element backing element(s) and preferably fibers on both outer faces of the hook element containing backing element(s) are entangled with each other. For example, a single given fiber could be found on both faces of a given strand and could also be entangled with other fibers on one or both faces of a given strand. The fibers with the embedded hook containing backing element are preferably not stratified as distinct layers, but a single integral web structure composite. This provides an integral hook element/nonwoven composite without the need for secondary bonding treatments such as adhesive or thermal bonding of the backing elements or strands to the nonwoven fibers.

The hook containing backing elements and the nonwoven are preferably coextensive along a longitudinal direction of the composite web and preferably are in some embodiments coextensive across the entire composite structure. This provides a composite that is dimensionally stable preferably at least in the longitudinal or transverse direction. When the hook backing elements comprise strands in a coherent net form, the composite generally has dimensional stability (as above) in at least two directions. The nonwoven coupled with the hook element containing backing elements or hook strands in an integral composite creates a self-engagable fastener that can engage with itself at substantially any location where the hook elements and the entangled nonwoven web are coextensive.

The formed hook fasteners fibrous composite is preferably extremely flexible and breathable where the flexibility of the composite is substantially that of the hook element containing backing element, for example, having a Gurley Stiffness less than 400 Gurley Stiffness units, preferably less than 200 Gurley Stiffness units. As adhesive or thermal lamination is not necessary, the hook elements are not be destroyed in the lamination process so that hook elements can be substantially uniformly and continuously distributed in a given longitudinal or transverse extent along a hook containing backing element either continuously or intermittently, which extents can be linear or nonlinear. The hooks are preferably uniformly distributed in all extends of the composite in a given direction containing the hook containing backing, and most preferably in both the longitudinal and transverse (or multiple) directions of the composite, for example, strands present in two or more directions.

The lack of adhesive or thermal bonding allows the formation of lofty composite with fibers extending on one or both sides of the hook containing backing elements or strands and preferably covering both faces of the backing elements or strands to provide a lofty self engaging composite.

In one embodiment, the hook containing backing element can be longitudinally or transversely, or otherwise extending, discrete or loosely connected linear or nonlinear strand elements having hook elements on at least one face. Longitudinally extended discrete strands could then be fed into the hydraulic entanglement process. With at least this embodiment, it is possible to form an elasticated hook fastener nonwoven composite by use of elastic woven or nonwoven webs. The entangled composite could then stretch between the strands due to an attached elastic web. If the strands are connected, but stretchable due to a loose connection, or if the strands are stretchable due to being nonlinear, elasticity could also be created. Some other types of backing elements, such as nettings, are stretchable or extensible in one or more directions, also permitting the creation of an elastic composite. Elasticity can also be created in a composite containing an extensible backing element and also having an extensible nonelastic web or nonwoven and incorporated into the composite. Elasticity can also be created by elastic strands on a web or the like having elasticity extending at an angle to the direction of extensibility of the backing elements and any attached nonwoven created on the elastic composite. Elasticity can also be created by using elastic hook containing strand elements embedded within an extensible nonwoven.

An elastic nonwoven web could be a separate web joined to an extensible nonwoven web in which the extensible backing element is embedded, or in whole or in part, where the elastic web can be located adjacent or between one or more pairs of hook containing backing elements, which are all embedded or entangled within a further nonwoven web. Examples of suitable nonwoven or woven elastic webs include spunbond elastic polyurethane and meltblown webs, elastic block copolymer meltblown webs, elastic netting, perforated elastic webs and the like. Elastic strands could also be used.

Figure 12A:
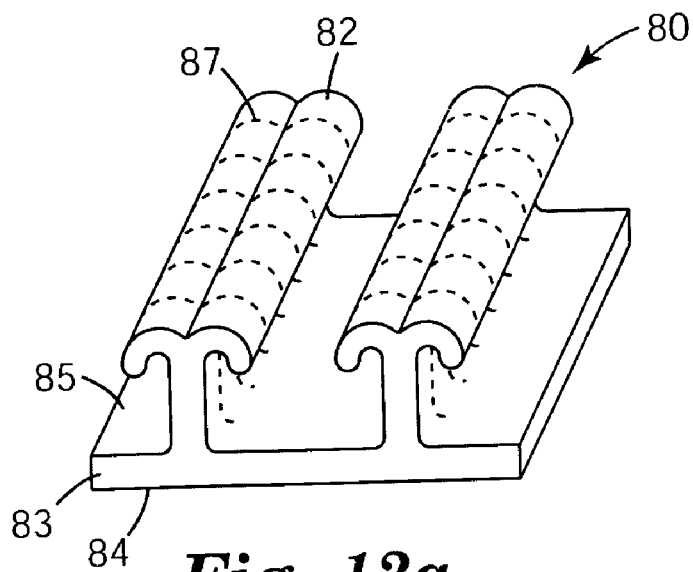
FIGS. 12(a)–12(c) are perspective views of various stages of forming a hook containing strands used in forming a fibrous hook fastener of the invention.
Figure 12B:
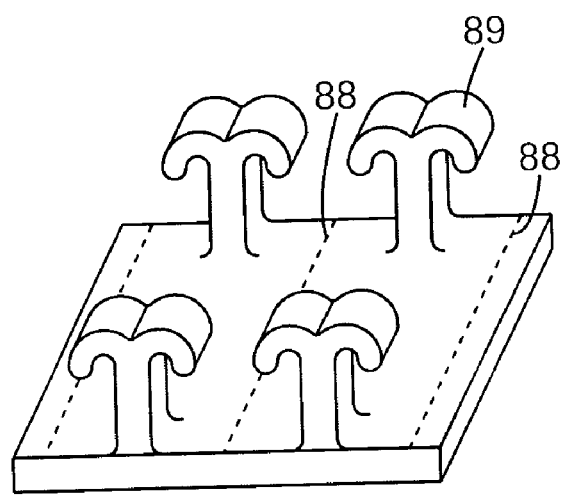
Figure 12C:
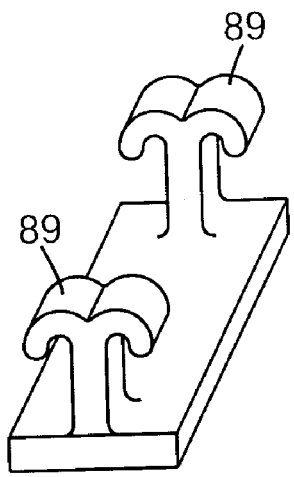

Individual discrete hook containing strands could be formed from a conventional hook film by longitudinal slitting, fibrillation or other separation processes. Preferred are hook films having a molecularly oriented backing in the longitudinal direction of the film to assist in the splitting or slitting of the film. The hook film could be split for example by water jets, rotating blades, lasers, etc., as is shown in FIGS. 12(a)–12(c). The hooks of FIG. 12(b) are formed from hook shaped ribs 82 on an extruded film backing 83, having a first face 85 and a second face 84 much like as in FIGS. 2, 3 and 4(a) however the hook shaped ribs are cut, not the backing. The rib cut portions 87 form the hook elements 89. The backing is oriented in the direction of the ribs 82 and then split along lines 88 to form discrete hook containing strands as shown in FIG. 12(c).

A first method of forming a hook containing netting useful in the invention is disclosed in U.S. Pat. No. 4,001,366 which describes forming hooks by extruding a backing and rib structures in having the basic shape of the hook (similar to the methods described in U.S. Pat. Nos. 4,894,060 and 4,056,593). A reticulated web or mesh structure is formed by intermittently slitting (skip slitting) the extruded ribs and bases and then pulling to expand the skip slit structure into a mesh or netting. The slit ribs form the hook elements.

U.S. Ser. No. 10/376,979 (3M Case No. 58313US002) the substance of which is incorporated by references in its entirety, discloses another method of making polymer hook containing netting by a novel adaptation of a known method of making hook fasteners as described, for example, in U.S. Pat. Nos. 3,266,113; 3,557,413; 4,001,366; 4,056,593; 4,189,809 and 4,894,060 or alternatively 6,209,177. This profiled extrusion method generally includes extruding a thermoplastic resin through a die plate, which die plate is shaped to form at least a base film layer and at least a first set of spaced ridges or ribs projecting above a first surface of the base layer. The spaced ridges or ribs formed by the die are used to form the first set of strands of a reticulated mesh or netting. The second set of transverse strands are formed by transversely cutting the base layer at spaced locations along a length, at a transverse angle to the ridges or ribs, to form discrete cut portions. Subsequently longitudinal stretching of the ridges (in the direction of the ridges or the machine direction) separates these cut portions of the backing, which cut portions then form the second set of spaced apart strands of the reticulated mesh or netting. The discrete hook elements are formed by providing at least a set of ribs or ridges having the basic profile of a hook element and slitting these ribs in the transverse direction and orienting the ribs transverse to the cut direction. These hook containing ribs or ridges could be some or all of the first set of ribs or ridges or could be a second set of ribs or ridges on the second face of the base layer.

The above film extrusion process creates hook element containing strands where the hook elements are created by cutting the ribs or ridges and generally stretching the backing or base layer. The basic hook cross-section is formed on the hook ribs by the profiled film extrusion die. The die simultaneously extrudes the film backing and the rib structures. The individual hook elements are then preferably formed from hook shaped ribs by cutting the hook shaped ribs transversely, followed by stretching the extruded film at least in the longitudinal direction of the cut hook shaped ribs. An uncut portion of the backing or the uncut ribs on the backing elongates and as such get thinner or smaller. However, the cut backing and/or the hook rib sections, between the cut lines remain substantially unchanged. This causes the individual cut sections of the hook shaped ribs to separate each from the other in the direction of elongation forming discrete hook elements. Alternatively, using this same type extrusion process, sections of the hook rib structures can be milled out to form discrete hook elements. With this profile extrusion process, the basic hook cross section or profile is only limited by the die shape.

These cut hook shaped ribs can also form the individual hook elements by partial transverse cutting of the ribs, which partially cut portions preferably have the base shape of the desired hook elements as described above. All the ribs will have an uncut portion in a preselected plane. The uncut portions of the hook shaped ribs will form strands, with discrete hook elements on them, when the film is stretched in the direction of the hook shaped ribs. A second set of transverse strands can then be formed by transversely cutting through the base film layer at spaced locations along a length, at a transverse angle to the hook shaped ribs, to form discrete cut portions. Subsequently longitudinal stretching of the ribs (in the direction of the ribs or the machine direction) separates these cut portions of the backing, which cut portions then form the second set of spaced apart strands of the reticulated mesh or netting. The uncut portions of the ribs elongate and form strands at an angle to the strands formed by the cut backing. The stretching also orients the uncut portion of the hook shaped ribs increasing their strength and flexibility.

Figure 2:
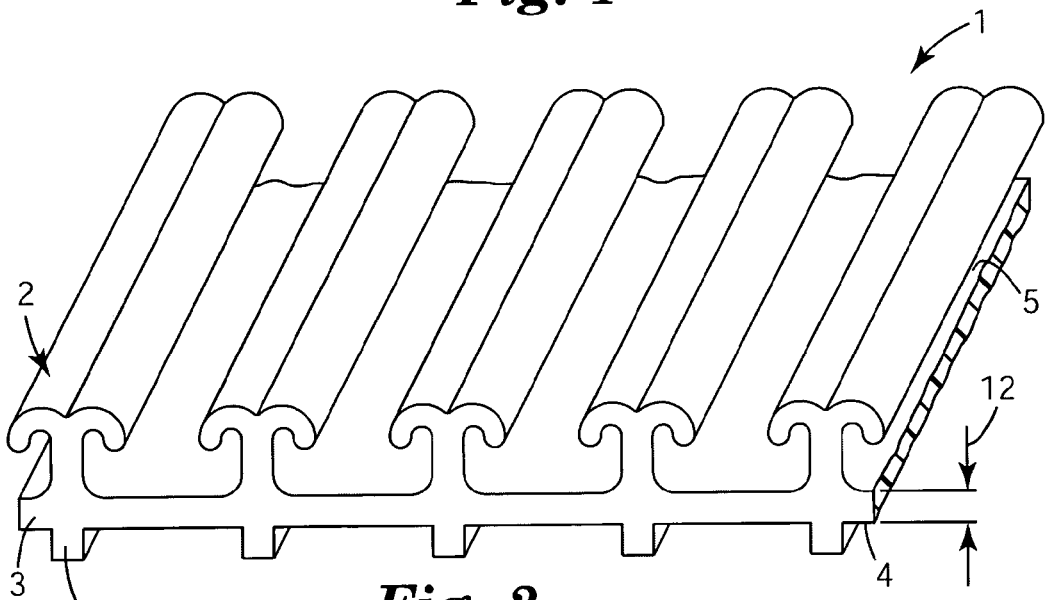
FIG. 2 is a perspective view of a precursor film used to make the hook netting of FIG. 4(a).
Figure 3:
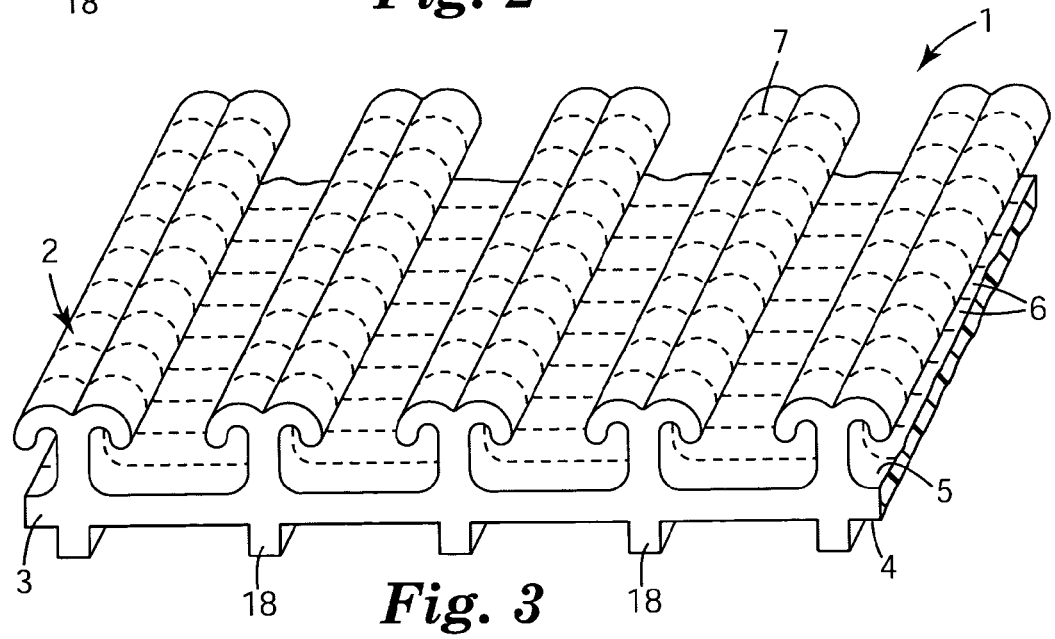
FIG. 3 is a perspective view of a first embodiment cut precursor film for forming a netting in accordance with the present invention.
Figure 6:
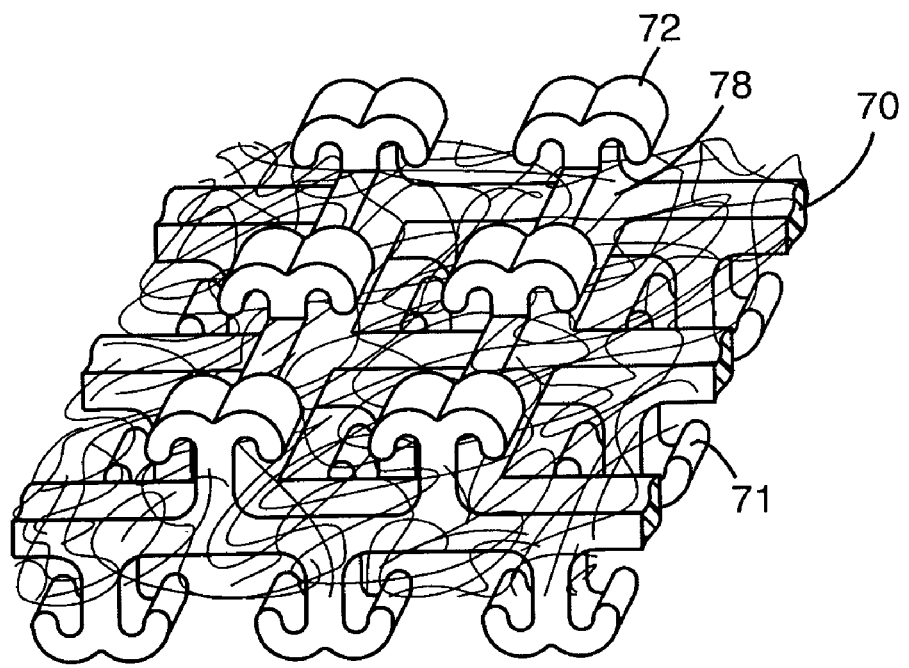
FIG. 6 is a schematic drawing of a second embodiment two-sided hook netting embedded into a fibrous web in accordance with the present invention.

The above method for forming a reticulated mesh or netting, such as that of FIGS. 4(a)–4(d), is schematically illustrated in FIG. 1. Generally, the method includes first extruding a strip 50 such as the strip 1, shown in FIG. 2, of thermoplastic resin from an extruder 51 through a die 52 having an opening cut, for example, by electron discharge machining, shaped to form the strip 50 with a base 3, and elongate spaced hook shaped ribs 2 projecting from at least one surface 5 of the base layer 3 that have a predetermined hook shaped cross sectional shape. As shown in FIGS. 2 and 3, the hook shaped ribs 2 have a structure similar to a hook element such as shown in FIGS. 4 and 6. If desired, a second set of ridges or ribs 18 can be provided on the second surface 4 of the base layer 3 which second set of ribs or ridges can have any predetermined shape, including that of a desired hook element 21 and 72 as shown in FIG. 6. The strip 50 is pulled around rollers 55 through a quench tank 56 filled with a cooling liquid (e.g., water), after which at least the base layer 3 is transversely slit or cut at spaced locations 7 along its lengths by a cutter 58 to form discrete portions 6 of the base layer 3. This would also require cutting of any ribs present on at least one face of the base layer. The distance between the cut lines 7 corresponds to about the desired width 11 of the strand portions 20 to be formed, as is shown in FIG. 4. The cuts 7 can be at any desired angle, generally from 90° to 30° from the lengthwise extension of the ribs 2 and/or 18. Optionally, the strip can be stretched prior to cutting to provide further molecular orientation to the polymers forming the base layer 3 or ribs 2 and/or 18 and reducing the size of the ridges or ribs 2 and/or 18 or base layer thickness 12 and also reducing the size of the strands 20 formed by slitting the base layer 3. The cutter 58 can cut using any conventional means such as reciprocating or rotating blades, lasers, or water jets, however preferably it cuts using blades oriented at an angle of about 60 to 90 degrees with respect to lengthwise extension of the ribs 2.

After cutting of the base layer 3 and the ridges or ribs 2 or ribs 18, the strip 1 is stretched at a stretch ratio of at least 1.5, and preferably at a stretch ratio of at least about 3.0, preferably between a first pair of nip rollers 60 and 61 and a second pair of nip rollers 62 and 63 driven at different surface speeds. This forms the first set of oriented strands 8 from ribs 18. Optionally, the strip 1 can also be transversely stretched to provide orientation to the strands 20 in their lengthwise extension. This basic method of extrusion, cutting (of at least the base layer) and stretching would generally apply to all embodiments of the invention. Roller 61 is preferably heated to heat the base 3 prior to stretching, and the roller 62 is preferably chilled to stabilize the stretched base 3. Stretching causes spaces 13 between the cut portions 6 of the base layer 3, which cut portions of the base layer then become the second set of strands 20 for the completed netting 14. The nonwoven web or webs is then fed, for example, from a roll 67, into the entanglement station 68 which embeds the hook netting within a fibrous web. A fibrous web could be applied to one or preferably both faces of the netting.

Figure 4A:
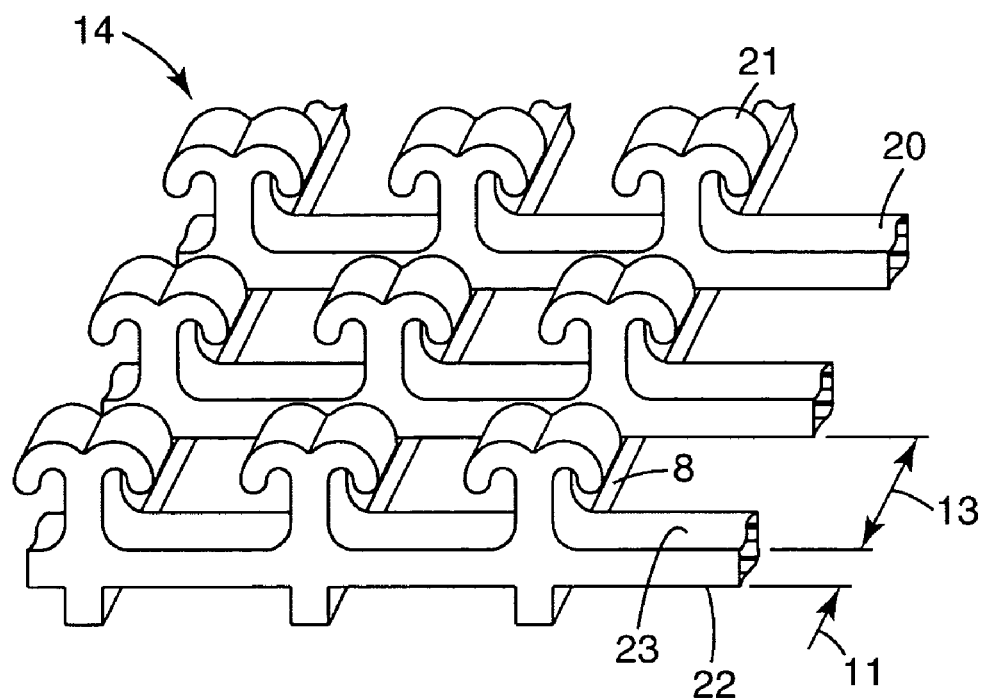
FIGS. 4(a)–4(d) are perspective views of various embodiments of a one sided hook netting in accordance with the present invention.
Figure 4B:
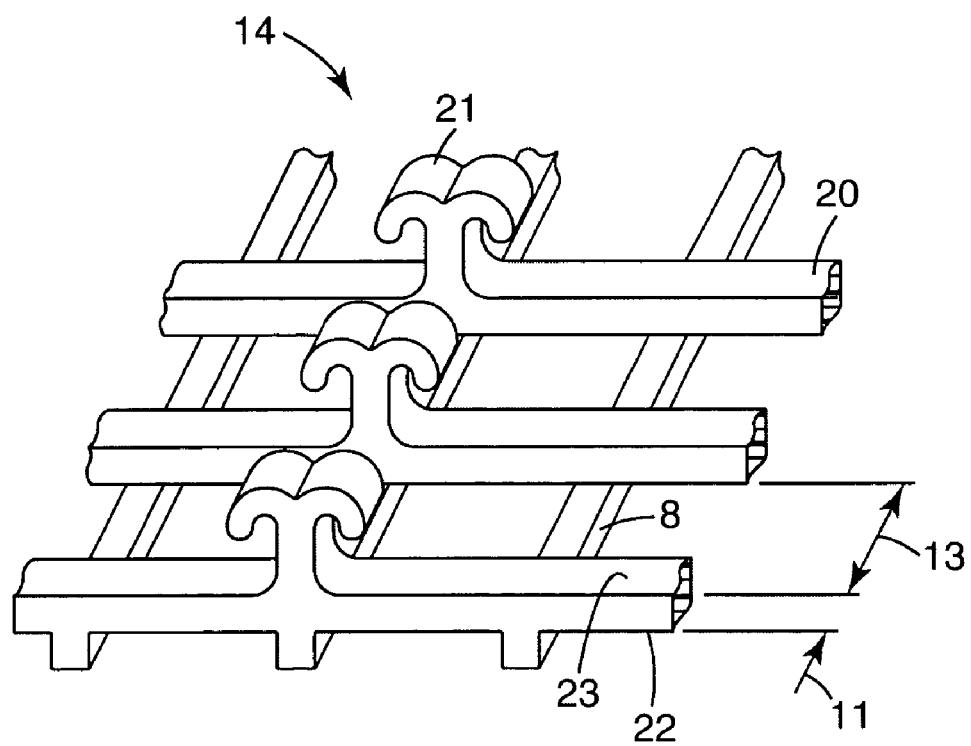
Figure 4C:
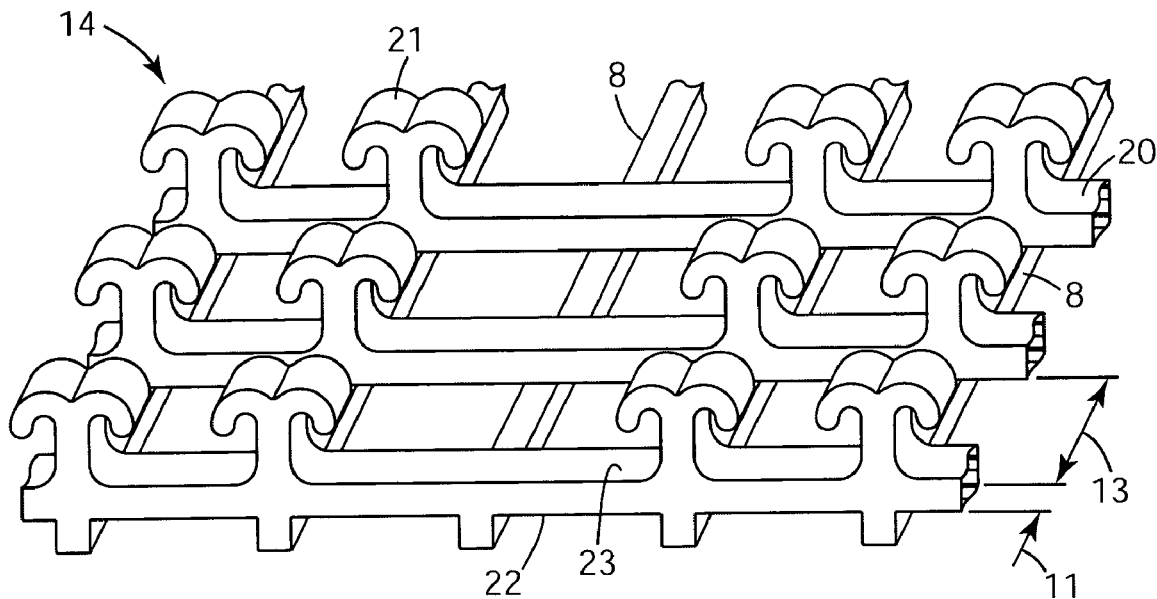
Figure 4D:
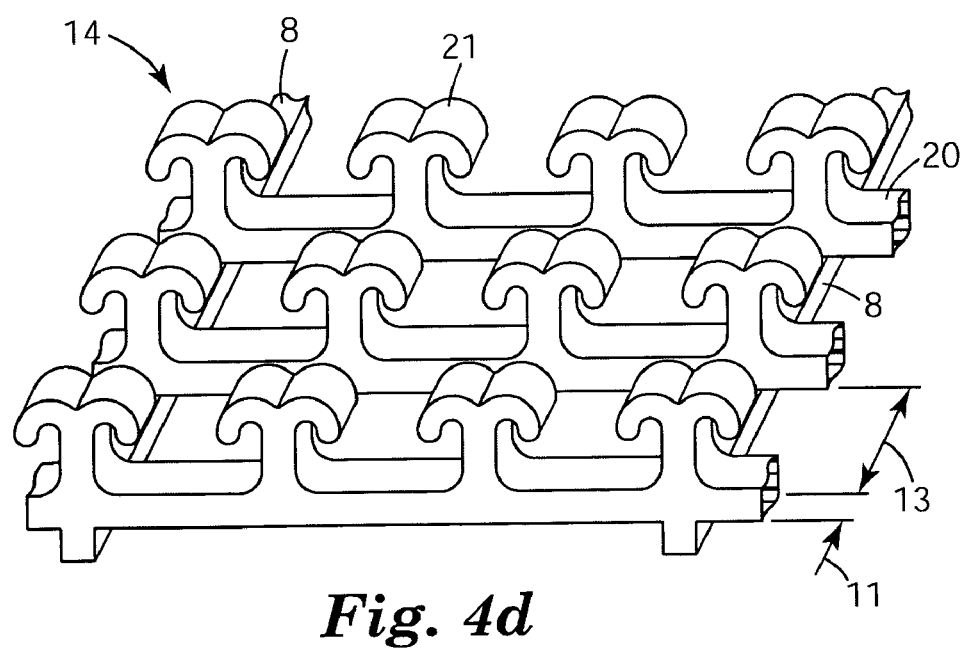

Referring to FIG. 4(a), an exemplary polymeric mesh hook fastener portion which can be produced, according to the present invention, generally designated by the reference numeral 14 is shown. The mesh hook netting comprises strands 20 having generally parallel upper and lower major surfaces 23 and 22, and a multiplicity of spaced hook members 21 projecting from at least the upper surface 23 of the strand 20. The strand 20 can have planar surfaces or surface features as could be desired for tear resistance or reinforcement. The strands 20 are separated from each other by cuts and elongation of ribs 18 into strands 8. FIG. 4(b) is a variation of the FIG. 4(a) embodiment where the hook members are more widely spaced and are not directly adjacent each strand member 8. The hook elements could also be created offset from strand members 8 and located between strands 8, as shown in FIG. 4(d), on strands 20. FIG. 4(c) is a further variation like FIG. 4(b). The absence of hook elements in certain areas of a netting or mesh as shown in FIGS. 4(b) and 4(c) would provide areas without hooks that would be more receptive to engage with other hooks as a loop surface or provide an area without hook elements for bonding to a further substrate, such as by thermal bonding or adhesives. The FIG. 4(d) embodiment could be used to form a hook fastener fibrous composite with discrete hook strands extending only in the transverse direction. The fibrous composite could be formed using the FIG. 4(d) material with the strands 8 stabilizing the strands 20 in the transverse direction while it is joined to the fibrous webs. The portions containing the strands 8 could then be trimmed away leaving only the strands 20 in the final hook fastener fibrous composite. This would be useful in certain applications.

Figure 5:
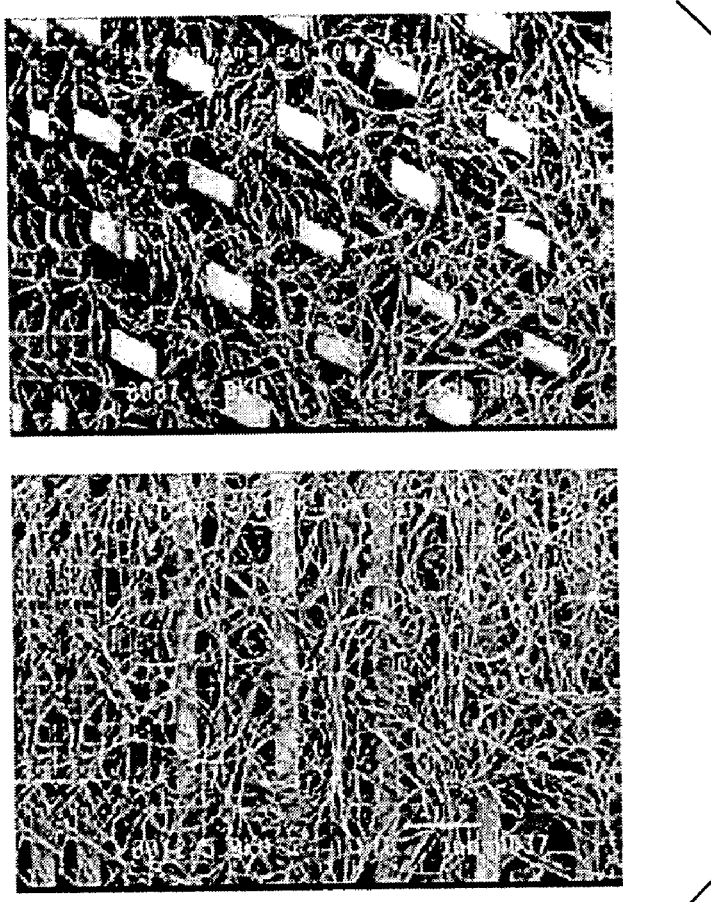
FIG. 5 are photomicrograph top and bottom views of a first embodiment hook netting such as in FIG. 4(a) embedded into a fibrous web in accordance with the present invention.

FIG. 5 shows the final hook fastener nonwoven composite where a hook netting, such as shown in FIG. 4(a), is embedded within nonwoven webs placed on both faces of the hook netting. The hook netting and nonwoven layers are not additionally bonded together by thermal bonding or adhesives.

Suitable polymeric materials from which the netting can be made include thermoplastic resins comprising polyolefins, e.g. polypropylene and polyethylene, polyvinyl chloride, polystyrene, nylons, polyester such as polyethylene terephthalate and the like and copolymers and blends thereof. Preferably the resin is a polypropylene, polyethylene, polypropylene-polyethylene copolymer or blends thereof.

An extruded hook netting is shown, within a hook fastener fibrous nonwoven composite, in FIG. 6 which netting has hook fastening elements on both faces of the netting. Generally, with a dual sided hook netting as shown in FIG. 6, the precursor film is formed with elongate spaced hook shaped ribs that project from both surfaces of the base layer, where each set of ribs has at least some ribs with a cross-sectional shape of the hook portions or members to be formed. The hook shaped ribs on one face are partially transversely slit at spaced locations along their lengths. The entire ribs and the base layer on the other face of the base layer are fully cut as per, e.g., the FIGS. 4 and 5 embodiments. When the partially cut hook shaped ribs are longitudinally elongated or stretched, as per the FIGS. 4 and 5 embodiments, they form hook elements 72 and oriented strands 78 (from the uncut portion of the ribs). Simultaneously with longitudinal stretching, the cut base layer and other set of ribs form transverse strands 70 and hook elements 71 on the strands 70.

Hook fastener fibrous nonwoven composites, such as shown in FIGS. 5 and 6, are highly breathable and dimensionally stable, in at least the direction of strands 18, 20, 70 or 78. Dimensional stability means that the netting will have essentially the same dimensions when untensioned and when placed under moderate tension in the direction of linearly extending strands (e.g., 8, 20, 70 and 78). Further, these fasteners would also be dimensionally stable in the more than one direction if there are intersecting linear strands at angles to each other. However, with intersecting linear strands, when stretched in a direction at an angle to both sets of linear strands, the netting and as such the composite will stretch, and in some cases will tend to elastically recover to its dimensionally stable form. The linear strands in both directions can be oriented to increase their mechanical strength and reduce their basis weight while increasing their flexibility and dimensional stability.

Figure 7:
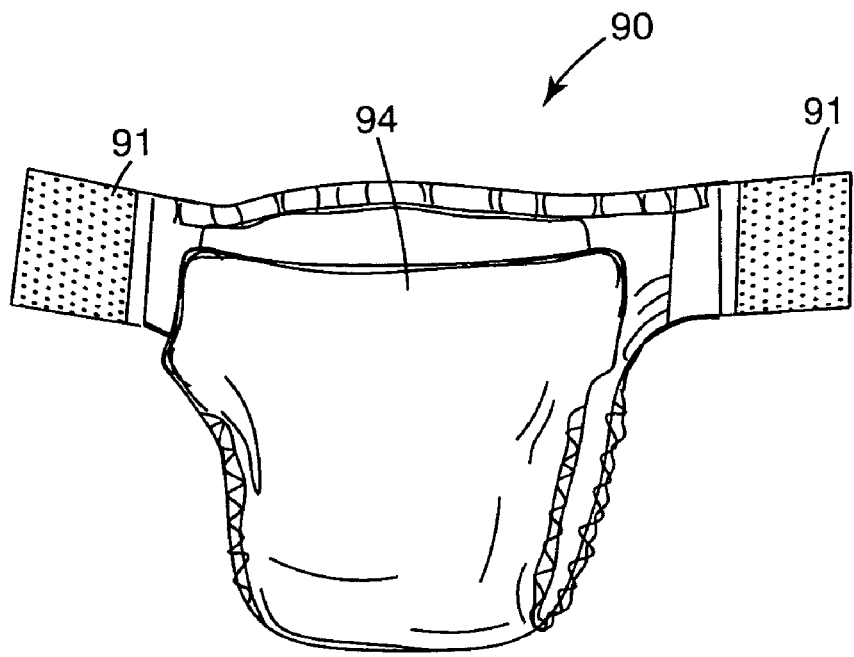
FIG. 7 is a perspective view of a disposable absorbent article including a fibrous hook fastener web of the invention.
Figure 8:
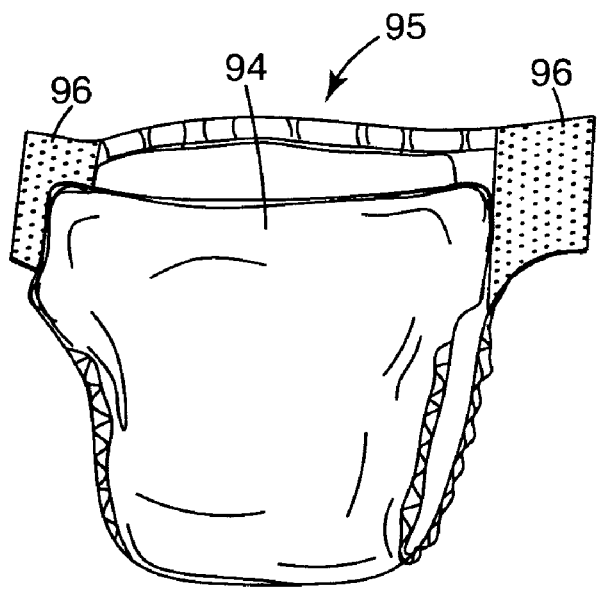
FIG. 8 is a perspective view of a second embodiment of a disposable absorbent article including a fibrous hook fastener web of the invention.
Figure 9:
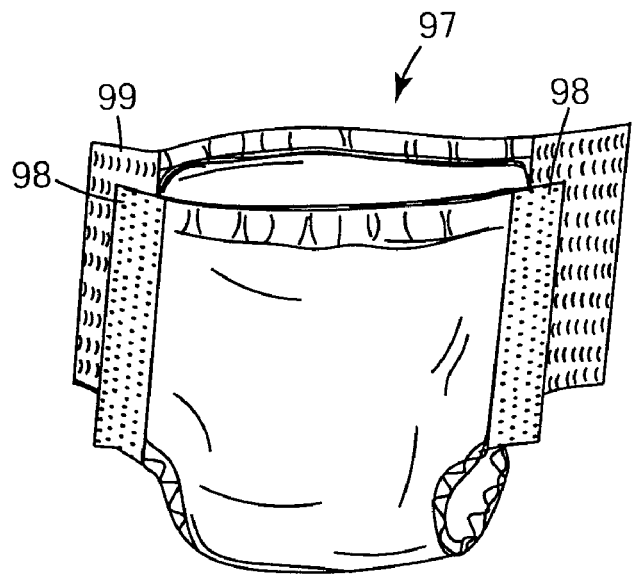
FIG. 9 is a perspective view of a third embodiment of a disposable absorbent article including a fibrous hook fastener web of the invention.

In a particularly preferred application, the invention hook fastener fibrous composite is self-mating with itself and as such is an extremely low cost and highly functional bundling material such as a bundling strap, a vegetable wrap, a medical wrap, a sport wrap or like applications where breathability and self engageability are important. The hook fastener fibrous composite in particular could find use in disposable garment applications such as headbands, diapers, incontinent briefs, feminine hygiene articles and the like where it is desirable to have an engaging material that would conform to a user and provide breathability. In these and other applications, the hook fastener composite could also be bonded to other structures, such as fibrous webs (e.g., nonwoven fibrous knitted or stitch bonded fibrous materials), films or three-dimensional structures by conventional techniques such as adhesive lamination, thermal or pressure welding ultrasonic bonding or combinations of these bonding techniques. A suitable use of the hook fibrous composite is on a diaper 90, as shown in FIG. 7, where a large area diaper fastening tab 91 is formed of the invention hook fastener fibrous composite. The hook fastener fibrous composite tab could be joined to the edge of the diaper by suitable bonding techniques such as heat, pressure, adhesives or sonic welding or any combination of bonding methods. The invention hook fastener fibrous composite could also be a continuous belt on the back section of the diaper and be made to join with itself to create a continuous belt fastener or fasten to a front portion 94 of the diaper such as by provision of a suitable fibrous material or loop on the outside face of the diaper. An alternative embodiment diaper 95 is shown in FIG. 8. In this case, the large area fastener is contoured to fit to the leg area of the wearer. In FIG. 9, a further embodiment diaper 97 has a side seam member 98, formed of the invention hook fastener fibrous composite which could engage with another side seam member 99, also formed of the invention hook fastener fibrous composite or a suitable mating loop structure.

Figure 10:
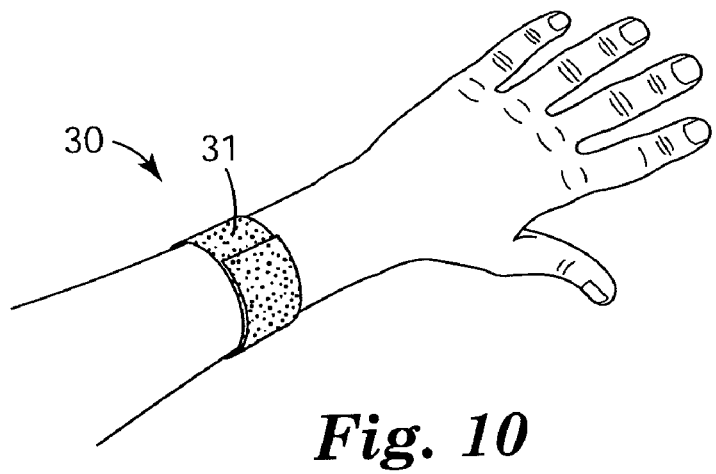
FIG. 10 is a perspective view of a wrap formed of the invention fibrous hook fastener web.

FIG. 10 is a wrap 31 formed as a self-engaging wrap of the invention hook fastener fibrous composite 31. The wrap could be used as a sports wrap or medical wrap or any other suitable use.

Figure 11:
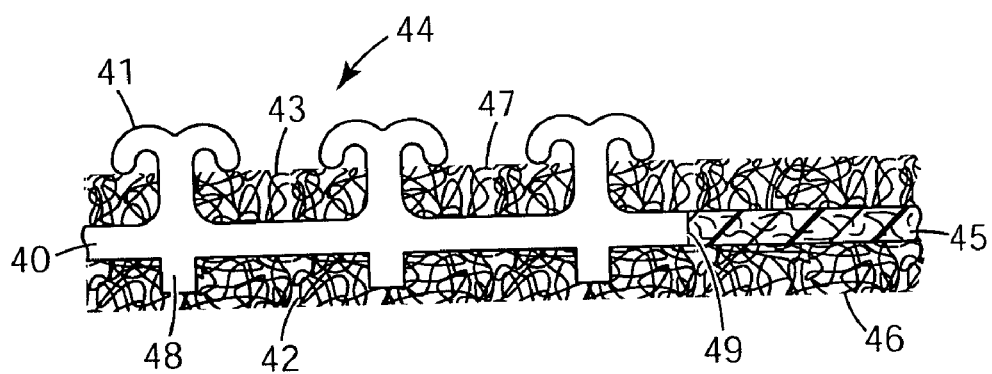
FIG. 11 is a side view of an elastic hook fastener web in accordance with the invention.

In FIG. 11, an alternative embodiment of a hook fastener fibrous composite is shown where an additional functional element 45 is joined to the composite adjacent to the hook element containing backing element 40. The hook element containing backing element as shown is a mesh type structure as shown in FIG. 4(*a*) with hook fastener elements 41 and longitudinally extending strands 48. The hook element containing backing element is embedded within two nonwoven webs 47 and 42 on both faces of the backing element 40. Adjacent the backing element is an additional foraminous or an open functional element 45 that has also been directly joined to one, or both, of the nonwoven webs 47 or 42 (indirect attachment is also possible). This additional functional element can be located directly adjacent 49 the backing element 40. The additional functional element can be entangled with the nonwoven web and can be a further netting, strands, woven or nonwoven material or the like. The additional functional element could also be attached by conventional bonding techniques such as thermal bonding, adhesive bonding or the like. As shown, this additional functional element is an elastic material so as to provide a hook composite having elastic properties. Other functional elements could include bonding layers, filter materials, reinforcing materials, reflective materials, etc.

EXAMPLE 1

A mesh hook netting was made using apparatus similar to that shown in FIG. 1. A polypropylene/polyethylene impact copolymer (SRC7-644, 1.5 MFI, Dow Chemical) was extruded with a 6.35 cm single screw extruder (24:1 L/D) using a barrel temperature profile of 175° C.-230° C.-230° C. and a die temperature of approximately 230° C. The extrudate was extruded vertically downward through a die having an opening cut by electron discharge machining to produce an extruded profiled web similar to that shown in FIG. 2. The crossweb spacing of the upper ribs was 7.3 ribs per cm. After being shaped by the die, the extrudate was quenched in a water tank at a speed of 6.1 meter/min with the water being maintained at approximately 10° C. The web was then advanced through a cutting station where the upper ribs and the base layer (but not the lower ribs) were transversely cut at an angle of 23 degrees measured from the transverse direction of the web. The spacing of the cuts was 305 microns. After cutting the upper ribs and the base layer, the web was longitudinally stretched at a stretch ratio of approximately 3 to 1 between a first pair of nip rolls and a second pair of nip rolls to further separate the individual hook elements to approximately 8.5 hooks/cm to produce a hook mesh netting similar to that shown in FIG. 4. The thickness of the base layer was 219 microns. The upper roll of the first pair of nip rolls was heated to 143° C. to soften the web prior to stretching. The second pair of nip rolls were cooled to approximately 10° C.

The tensile strength of the hook netting was measured by cutting a 1.3 cm wide sample in the longitudinal, downweb direction of the web. There were 11–12 strands in the test samples. The break tensile strength was measured using an INSTRON tensile tester. Five replicates were run and averaged together. The break tensile strength of the web was 4.91 kg/cm and 0.55 kg/strand.

The hook netting was then hydroentangled with two nonwoven webs by sandwiching the hook netting in between two 30 g/m² unbonded carded webs; each web consisting of 70% Wellman T310 1.5d polyester fibers, 25% Lyocell 1.5d rayon fibers and 5% Kosa T254 2d polyester bicomponent staple fibers. A conventional hydraulic entangling system consisting of 6 manifolds/jets (3 above and 3 below the web) was used. The basic operating procedure is described in, for example, U.S. Pat. No. 5,389,202, issued Feb. 14, 1995, to Everhart et al., the contents of which are incorporated herein by reference. Each manifold had an orifice size of 120 microns diameter. Orifices were positioned in a single row at a spacing of about 16 orifices per linear centimeter of manifold. Manifold water pressure was successively ramped up to 127 kg/cm$^2$ which generated high energy fine columnar jets. The hydraulic entangling surface was a single layer 100 stainless steel twill wire backing manufactured by Albany International, Portland, Tenn. The netting and two carded webs were passed under the manifolds at a line speed of about 10 meters per minute where they were washed and consolidated by the pressurized jets of water. The resulting composite web was dried utilizing a conventional laboratory handsheet dryer. The composite web had a cloth-like feel and appearance, and was very flexible and conformable.

EXAMPLE 2

A hydroentangled composite web was made similar to that in Example 1 except the two nonwoven unbonded carded webs consisted of a blend of 95% Kosa T224 3d polyester fibers and 5% Kosa T254 2d polyester bicomponent fibers. The basis weight of the carded webs was 30 grams/meter$^2$. The composite web had a cloth-like feel and appearance, and was very flexible and conformable.

EXAMPLE 3

A hydroentangled composite web having elastic properties was produced similar to the web in Example 1 except an additional elastomeric nonwoven web was used and a fibrillated hook material was used in place of the hook netting.

A hook web, available from 3M Company St. Paul, Minn. as KN-3425, was fibrillated using the following procedure. A 10 cm wide hook web was fed into a rotary cutting apparatus similar to that shown in FIG. 1 of U.S. Pat. No. 5,058,472. The apparatus consisted of intermeshing upper and lower steel rotary cutting rolls fitted with continuous cutting blades mounted around the periphery of the rolls. Spacers were used in between the blades to provide approximately 6 blades/cm in the lateral direction. The apparatus was operated manually with a hand crank to advance the hook web through the nip of the cutting apparatus at a nip pressure of approximately 70 kg/cm$^2$ to introduce slits through the web in the down web direction. Due to the input web being thicker in the hook regions and thinner in the non-hook regions, the cuts were intermittent rather than continuous in the downweb direction. The cut web was then further slit into 2.5 cm wide strips.

A four component hydroentangled composite (FIG. 11) was then produced using the procedure and apparatus described in Example 1. To provide elasticity to the composite a polyurethane (PUR) spunbond nonwoven web (50 g/m$^2$, UHF-50, Kanebo) was hydroentangled with the fibrillated hook web and sandwiched between 2 carded polyester webs (33 g/m$^2$, 140-070, BBA Nonwovens, Simpsonville, N.C.).

EXAMPLE 4

A hook web, similar to that shown in FIG. 3, available from 3M Company St. Paul, Minn. as KN-3425, was fibrillated using the following procedure. The hook web was fed into the hydraulic entangling system described in Example 1 at 2.5 m/min with the hook side facing downwards. Four jets positioned above the web were used at a pressure of 204 Kg/cm$^2$, to split the hook web from the backside, into nearly discrete strands, each strand containing a row of hooks. A polyester nonwoven web (34 g/m$^2$, 140-070, BBA Nonwovens) was then laminated to the hook side of the fibrillated hook web using 3 jets positioned below the webs at a water pressure of 61 Kg/cm$^2$. The composite was then wound into a roll and dried. The composite was then stretched by hand in the cross-direction approximately 2:1 and fed into the hydraulic entangling apparatus at 2.5 m/min along with an additional nonwoven web (140-070) on the non-hook side of the web. The composite was hydroentangled together using 4 jets positioned above the web and 3 jets positioned below, all operating at 102 Kg/cm$^2$ of water pressure.

EXAMPLE 5

A hydroentangled composite was made using the following materials. A hook web (KN-3425) was slit in the downweb direction into 0.8 mm wide discrete strands and wound onto a common core. A 4 layer composite consisting of a nonwoven web (140-070)/slit hook web (KN-3425)/spunbond PUR (UHF-50)/nonwoven web (140-070) was fed into the hydraulic entangling apparatus described above at 10 m/min. The slit hook web was fed into the apparatus as 2.5 cm strips spaced approximately 10 cm apart. The composite was hydroentangled together using 4 jets positioned above the web and 3 jets positioned below, all operating at 153 Kg/cm$^2$ of water pressure.

We claim:

1. A hook fastener composite comprising a backing element having a first outer face and a second outer face, and hook elements extending from at least one outer face wherein the backing element is embedded within a single integral fibrous web such that fibers of the web are present on both outer faces of the backing element.

2. The hook fastener composite of claim 1 wherein the hook containing backing element at least has strand elements containing hook elements.

3. The hook fastener composite of claim 1 wherein the hook containing backing element comprises discrete hook containing strands.

4. The hook fastener composite of claim 2 wherein the strand elements extend in at least one direction.

5. The hook fastener composite of claim 4 wherein the strand elements extend linearly in at least the at least one direction.

6. The hook fastener composite of claim 4 wherein the strands are parallel to each and extend in the longitudinal direction of the composite.

7. The hook fastener composite of claim 1 wherein the fibrous web is a nonwoven fibrous web.

8. The hook fastener composite of claim 7 where in the nonwoven fibrous web has a basis weight of from 10 to 500 g/m$^2$.

9. The hook fastener composite of claim 7 wherein the nonwoven fibrous web is substantially unbonded by secondary bonding means.

10. The hook fastener composite of claim 7 wherein the nonwoven fibrous web is an unbonded carded nonwoven web.

11. The hook fastener composite of claim 7 wherein the composite is an elastic composite.

12. The hook fastener composite of claim 1 wherein the composite has an elastic element located adjacent the backing elements.

13. The hook fastener composite of claim 12 wherein the elastic element is a foraminous elastic.

14. The hook fastener composite of claim 13 wherein the elastic element is entangled with the fibrous web.

15. The hook fastener composite of claim 13 wherein the elastic element is a fibrous web.

16. The hook fastener composite of claim 2 wherein a second set of strands extend in a direction transverse to the first set of strands and the two sets of strands are joined at their crossover points forming a netting and the first set of strands are oriented strands.

17. The hook fastener composite of claim 16 wherein said second set of strands are mutually parallel and have a first face and a second face and two substantially parallel side faces and are substantially coextensive.

18. The hook fastener composite of claim 16 wherein said second set of strands second faces are attached to said first set of oriented strands at their crossover points.

19. The hook fastener composite of claim 16 wherein said first set of strands occupy a first planar cross-sectional area in the thickness direction of the netting and said second set of oriented strands occupy a second planar cross-sectional area in the thickness direction of the netting.

20. The hook fastener composite of claim 19 wherein said first and second planar cross-sectional areas are substantially mutually exclusive and abutting.

21. The hook fastener composite of claim 16 wherein said second set of strands have a substantially rectilinear cross-section.

22. The hook fastener composite of claim 16 wherein said second set of strands are linear.

23. The hook fastener composite of claim 21 wherein adjacent strands of said second set of strands have a substantially identical cross-sectional shape in said first direction.

24. The hook fastener composite of claim 16 wherein said second set of strands have surface structures on said first faces of the strands.

25. The hook fastener composite of claim 24 wherein said surface structures are stems extending upward.

26. The hook fastener composite of claim 25 wherein said stem structures have hook elements projecting in at least one direction.

27. The hook fastener composite of claim 26 wherein said hook elements extend in the same direction of the second set of strands.

28. The hook fastener composite of claim 26 wherein said hook elements extend in two or more directions and form a mushroom shape.

29. The hook fastener composite of claim 16 wherein said first set of strands have surface structures on said second face of said strands.

30. The hook fastener composite of claim 29 wherein said surface structures are stems extending upward.

31. The hook fastener composite of claim 16 wherein said first and second set of strands are integrally formed.

32. The hook fastener composite of claim 31 wherein said polymer is a thermoplastic polymer.

33. The hook fastener composite of claim 1 wherein there is an additional foraminous layer entangled with the fibrous web.

34. An article comprising a closure element formed of a hook fibrous composite comprising a plurality of strands extending in a first direction the strands having a first outer face and a second outer face and two side faces, and hook elements extending from at least one outer face wherein there the strands are embedded within a single integral fibrous web such that fibers of the web are present on both outer faces of the strands.

35. A wrap comprising hook composite comprising a plurality of strands extending in a first direction the strands having a first outer face and a second outer face and two side faces, and hook elements extending from at least one outer face wherein there the strands are embedded within a single integral fibrous web such that fibers of the web are present on both outer faces of the strands.

36. The wrap of claim 35 wherein the wrap is self engaging.

* * * * *